(12) United States Patent
Pan

(10) Patent No.: US 11,554,198 B1
(45) Date of Patent: Jan. 17, 2023

(54) INTEGRATED BREAST PUMP

(71) Applicant: SHENZHEN LUTEJIACHENG NETWORK TECHNOLOGY CO., LTD., Shenzhen (CN)

(72) Inventor: Silin Pan, Shenzhen (CN)

( * ) Notice: Subject to any disclaimer, the term of this patent is extended or adjusted under 35 U.S.C. 154(b) by 0 days.

(21) Appl. No.: 17/653,502

(22) Filed: Mar. 4, 2022

(30) Foreign Application Priority Data

Feb. 22, 2022 (CN) .......................... 202210160786.8

(51) Int. Cl.
*A61M 1/06* (2006.01)

(52) U.S. Cl.
CPC .............. *A61M 1/062* (2014.02); *A61M 1/067* (2021.05); *A61M 2205/3337* (2013.01); *A61M 2205/8206* (2013.01)

(58) Field of Classification Search
CPC ......... A61M 1/067; A61M 1/06; A61M 1/062
See application file for complete search history.

(56) References Cited

U.S. PATENT DOCUMENTS

| | | | |
|---|---|---|---|
| 2013/0023821 A1* | 1/2013 | Khalil | ..................... A61M 1/82 604/74 |
| 2017/0080135 A1* | 3/2017 | Chen | ..................... A61M 1/062 |
| 2018/0154055 A1* | 6/2018 | Alvarez | .................. A61M 1/82 |
| 2018/0361040 A1* | 12/2018 | O'Toole | ................ A61M 1/062 |
| 2021/0093761 A1* | 4/2021 | Hwang | ................ A61M 39/10 |

FOREIGN PATENT DOCUMENTS

KR 102296715 B1 * 9/2021

OTHER PUBLICATIONS

English translation of Hwang (KR 102296715) (Year: 2021).*

* cited by examiner

*Primary Examiner* — Nathan R Price
*Assistant Examiner* — Courtney B Fredrickson

(57) ABSTRACT

An integrated breast pump includes a housing, a triple valve integrated with the housing, a breast adapter, a negative pressure generation device, a negative pressure transmission element and an one-way valve. The triple valve includes a liquid inlet, a liquid outlet and a negative pressure port. The breast adapter includes a liquid guiding outlet and is detachably connected with housing. The liquid guiding outlet communicates with the liquid inlet. The negative pressure generation device includes a pumping port and is configured for providing negative pressure periodically. The negative pressure generation device is detachably connected with housing, and the pumping port is disposed towards the negative pressure port. The negative pressure transmission element is disposed in the negative pressure port and communicates with the pumping port. The negative pressure transmission element is configured for generating deformation periodically according to the negative pressure. The one-way valve is connected with the liquid outlet.

17 Claims, 7 Drawing Sheets

INTEGRATED BREAST PUMP

This application claims priority of Chinese Patent Application No. 202210160786.8, entitled "INTEGRATED BREAST PUMP" filed on Feb. 22, 2022, the entire contents of which are incorporated by reference herein.

FIELD

The present disclosure relates to a breast pump, and specifically to an integrated breast pump.

BACKGROUND

A breast pump is a device used to pump breast milk that has accumulated in a breast when a baby is unable to suck directly. The breast pump can not only liberate women, so that women can not only get relaxed in the lactation period to participate in social life and work, but also can help baby to suck breast milk easily, and can effectively observe the baby's food intake and help the baby adapt to milk bottle.

While existing electric breast pumps benefits a lot, there are some problems, such as the existing electric breast pumps have lots of components, the manufacturing process is complex and the cost is high. Moreover, due to the lots of components, the existing electric breast pumps have unstable structure, and air tightness between multiple connected components can not be guaranteed, it is easy to leak, affect the normal use of the existing electric breast pumps. Furthermore, some existing electric breast pumps take up large space, it is inconvenient to carry and complex to use, and user experience is poor.

Therefore, the present disclosure provides an integrated breast pump, which can effectively solve the problems listed above.

SUMMARY

In order to overcome the disadvantage of the existing electric breast pump, the present disclosure provides an integrated breast pump that can improve user experience.

The present disclosure provides an integrated breast pump including: an integrated breast pump including a housing; a triple valve integrated with the housing, the triple valve including a liquid inlet, a liquid outlet and a negative pressure port; a breast adapter with a funnel shape, the breast adapter including a liquid guiding outlet, the breast adapter detachably connected with housing, the liquid guiding outlet communicating with the liquid inlet; a negative pressure generation device including a pumping port configured for providing negative pressure periodically, the negative pressure generation device detachably connected with housing, the pumping port disposed towards the negative pressure port; a negative pressure transmission element disposed in the negative pressure port, the negative pressure transmission element communicating with the pumping port and configured for generating deformation periodically according to the negative pressure; and an one-way valve connected with the liquid outlet.

Further, a surface of the housing includes an accommodating groove, the negative pressure port is disposed on a bottom part of the accommodating groove, and the negative pressure transmission element is disposed in the the accommodating groove.

Further, an edge of the negative pressure transmission element includes a first restriction groove, and a side wall of the accommodating groove is inserted into the first restriction groove.

Further, a surface of the negative pressure generation device includes a fixing block, a second restriction groove is formed between the fixing block and a housing of the negative pressure generation device, and a side wall of the first restriction groove is fixed in the second restriction groove.

Further, the one-way valve is disposed on an upper surface of the breast adapter and protrudes from the upper surface of the breast adapter, and when the breast adapter is connected with the housing, the one-way valve covers the liquid outlet.

Further, a first restriction block is disposed on an edge of the housing and protrudes from the edge of the housing, a third restriction groove is disposed on an edge of the breast adapter, and the first restriction block is inserted in the third restriction groove.

Further, a fourth restriction groove is disposed on an upper surface of the breast adapter, a second restriction block is disposed on a surface of the triple valve, and the second restriction block is inserted in the fourth restriction groove.

Further, a third restriction block is disposed on the housing, a restriction platform is disposed on a surface of the negative pressure generation device, and the third restriction block abuts against the restriction platform.

Further, the negative pressure generation device includes an accommodation housing, a battery and a pump, the pump is electrically connected to the battery, and the battery and the pump are disposed in the accommodation housing.

Further, a charging port is disposed on a surface of the accommodation housing, and the charging port is electrically connected to the battery.

Further, the negative pressure generation device includes a control board and at least one button, the control board is disposed in the accommodation housing, and the control board is electrically connected to the battery and the pump, the button is disposed on the surface of the accommodation housing, and the button is electrically connected to the control board.

Further, the one-way valve is integrated with the breast adapter.

Further, an outer surface of the housing is curved so that the outer surface of the housing is able to fit on an inner surface of a bra of the user.

Further, the breast adapter is made of silicone; the negative pressure transmission element 40 is made of silicone.

The present disclosure also provides an integrated breast pump including a housing; a triple valve integrated with the housing, the triple valve including a liquid inlet, a liquid outlet and a negative pressure port; a breast adapter with a funnel shape, the breast adapter including a liquid guiding outlet, the breast adapter detachably connected with housing, and a liquid accommodation space formed by the breast adapter and the housing, the liquid guiding outlet communicating with the liquid inlet; a negative pressure generation device including a pumping port configured for providing negative pressure, the negative pressure generation device detachably connected with housing, the pumping port disposed towards the negative pressure port; a negative pressure transmission element disposed in the negative pressure port, the negative pressure transmission element communicating with the pumping port and configured for generating deformation according to the negative pressure; and an one-way valve connected between the liquid outlet and the liquid accommodation space.

Further, a surface of the housing includes an accommodating groove, the negative pressure port is disposed on a bottom part of the accommodating groove, and the negative pressure transmission element is disposed in the the accommodating groove.

Further, an edge of the negative pressure transmission element includes a first restriction groove, and a side wall of the accommodating groove is inserted into the first restriction groove.

Further, a surface of the negative pressure generation device includes a fixing block, a second restriction groove is formed between the fixing block and a housing of the negative pressure generation device, and a side wall of the first restriction groove is fixed in the second restriction groove.

Further, the one-way valve is disposed on an upper surface of the breast adapter and protrudes from the upper surface of the breast adapter, and when the breast adapter is connected with the housing, the one-way valve covers the liquid outlet.

Further, a first restriction block is disposed on an edge of the housing and protrudes from the edge of the housing, a third restriction groove is disposed on an edge of the breast adapter, and the first restriction block is inserted in the third restriction groove; a fourth restriction groove is disposed on an upper surface of the breast adapter, a second restriction block is disposed on a surface of the triple valve, the second restriction block is inserted in the fourth restriction groove; a third restriction block is disposed on the housing, a restriction platform is disposed on a surface of the negative pressure generation device, and the third restriction block abuts against the restriction platform.

The present disclosure also has the beneficial effects: through the above structure, the triple valve is integrated with the housing, so that the integrated breast pump has a compact and stable structure, a bottom surface of the funnel shaped breast adapter can contact with a breast of a user to bring users comfortable experience, and the funnel shaped breast adapter and the housing form a liquid accommodation space. The liquid accommodation space can accommodate breast milk, there is no need to use a milk bottle for accommodating breast milk, such that the integrated breast pump has a high space utilization and a small size. The negative pressure generation device is connected with housing, the negative pressure transmission element can transmit the negative pressure periodically, there is no need to use guiding pipes, thus it is convenience to carry and use. It can be understood, the integrated breast pump has a simple and compact structure, a reasonable design, and a small size, it is easy to carry and use, user experience can be improved.

BRIEF DESCRIPTION OF THE DRAWINGS

For the purpose of a clearer description of the embodiments in this application or technical solutions in prior art, below is a brief introduction of the attached drawings needed to be used in the description of the embodiments or prior art. Apparently, the attached drawings in the following description are only some embodiments indicated in the present application. For ordinary skill in the art, they may obtain other drawings according to these attached drawings without any innovative laboring.

The present disclosure will be further described with reference to the attached drawings and the embodiments hereunder.

DETAILED DESCRIPTION

In order to provide a clear understanding of the objects, features, and advantages of the embodiments, the following are detailed and complete descriptions to the technological solutions adopted in the embodiments. Obviously, the descriptions are part of the whole embodiments. The other embodiments which are not processed creatively by technicians of ordinary skills in the field are under the protection of this disclosure. The same is given with reference to the drawings and specific embodiments. It should be noted that non-conflicting embodiments in the disclosure and the features in the embodiments may be combined with each other without conflict.

In the following description, numerous specific details are set forth in order to provide a full understanding of the disclosure. The disclosure may be practiced otherwise than as described herein. The following specific embodiments are not to limit the scope of the disclosure.

Unless defined otherwise, all technical and scientific terms herein have the same meaning as used in the field of the art as generally understood. The terms used in the disclosure are to describe particular embodiments and are not intended to limit the disclosure.

The disclosure, referencing the accompanying drawings, is illustrated by way of examples and not by way of limitation. It should be noted that references to "an" or "one" embodiment in this disclosure are not necessarily to the same embodiment, and such references mean "at least one."

Figure 1:
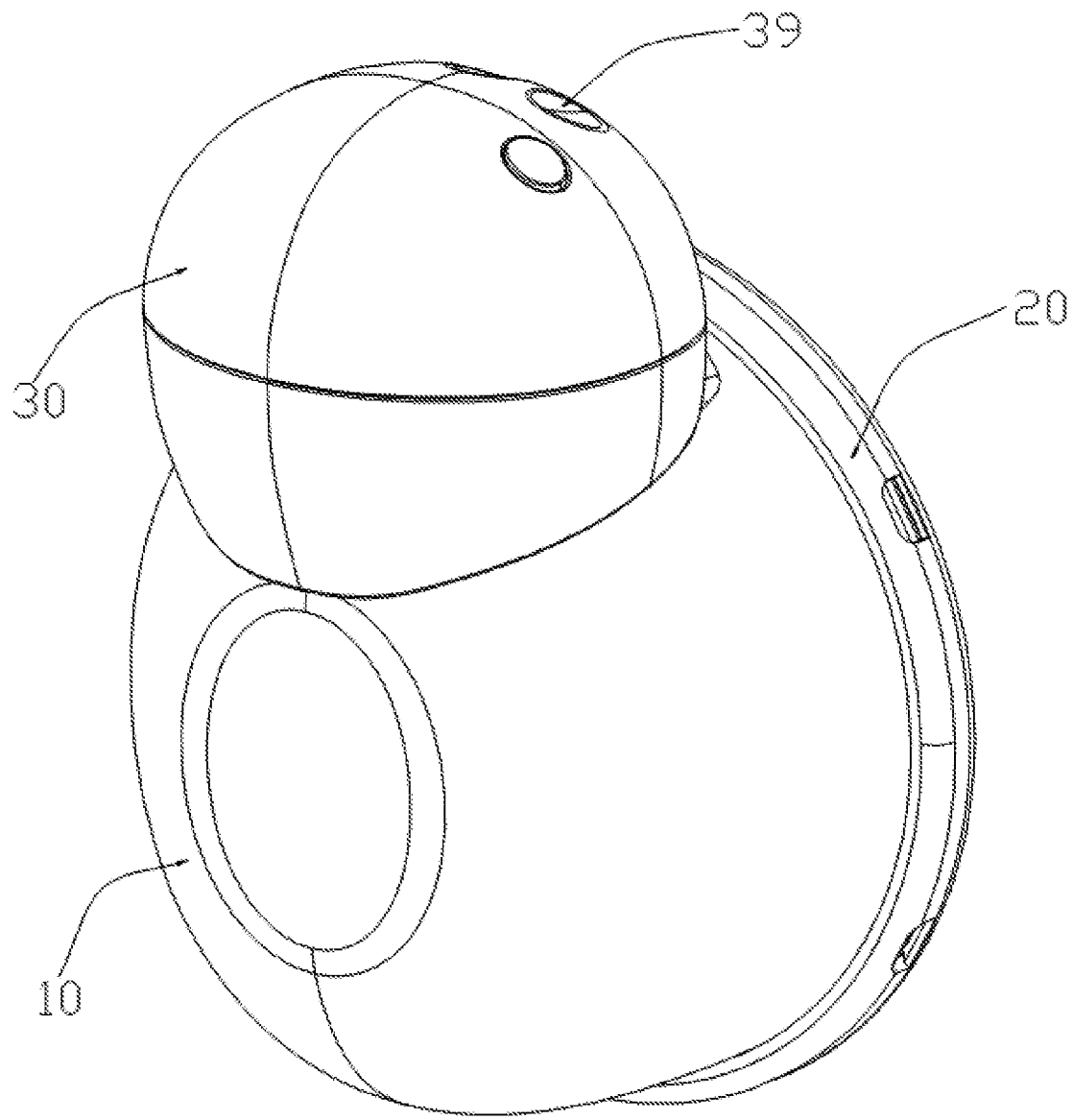
FIG. 1 is a schematic view of an integrated breast pump according to an embodiment of the present disclosure.
Figure 2:
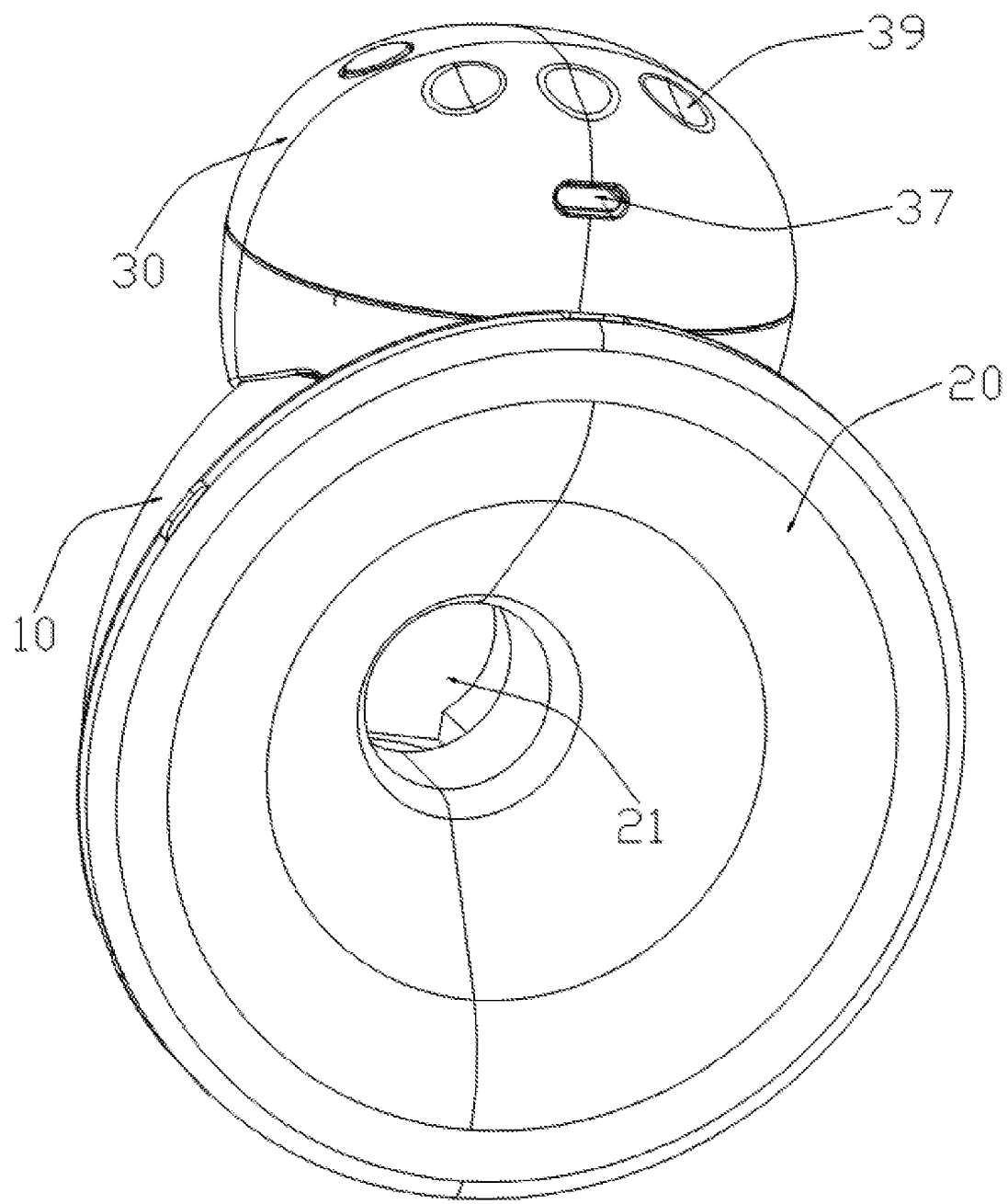
FIG. 2 is another schematic view of the integrated breast pump of FIG. 1.
Figure 3:
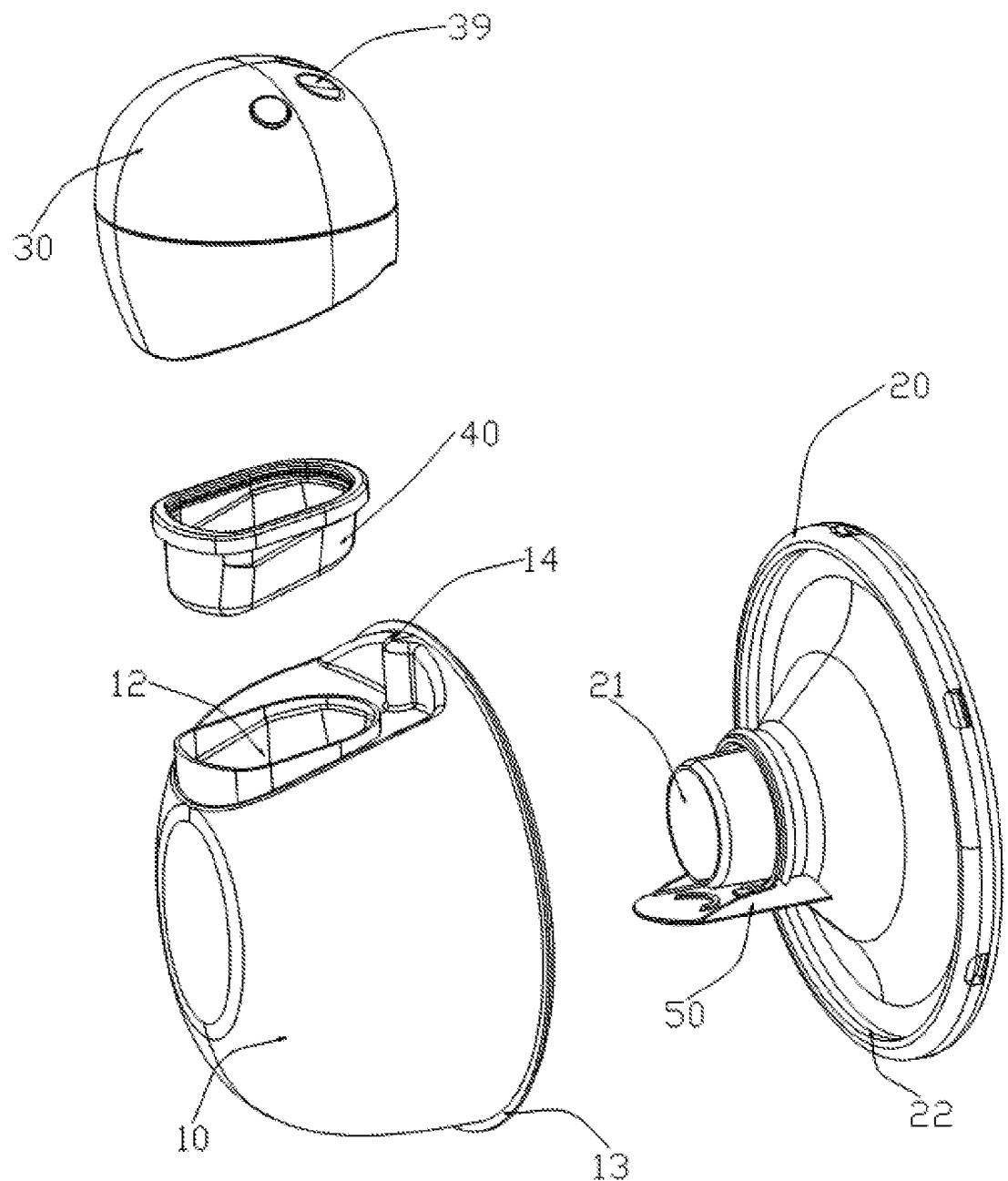
FIG. 3 is an exposed view of the integrated breast pump of FIG. 1.
Figure 4:
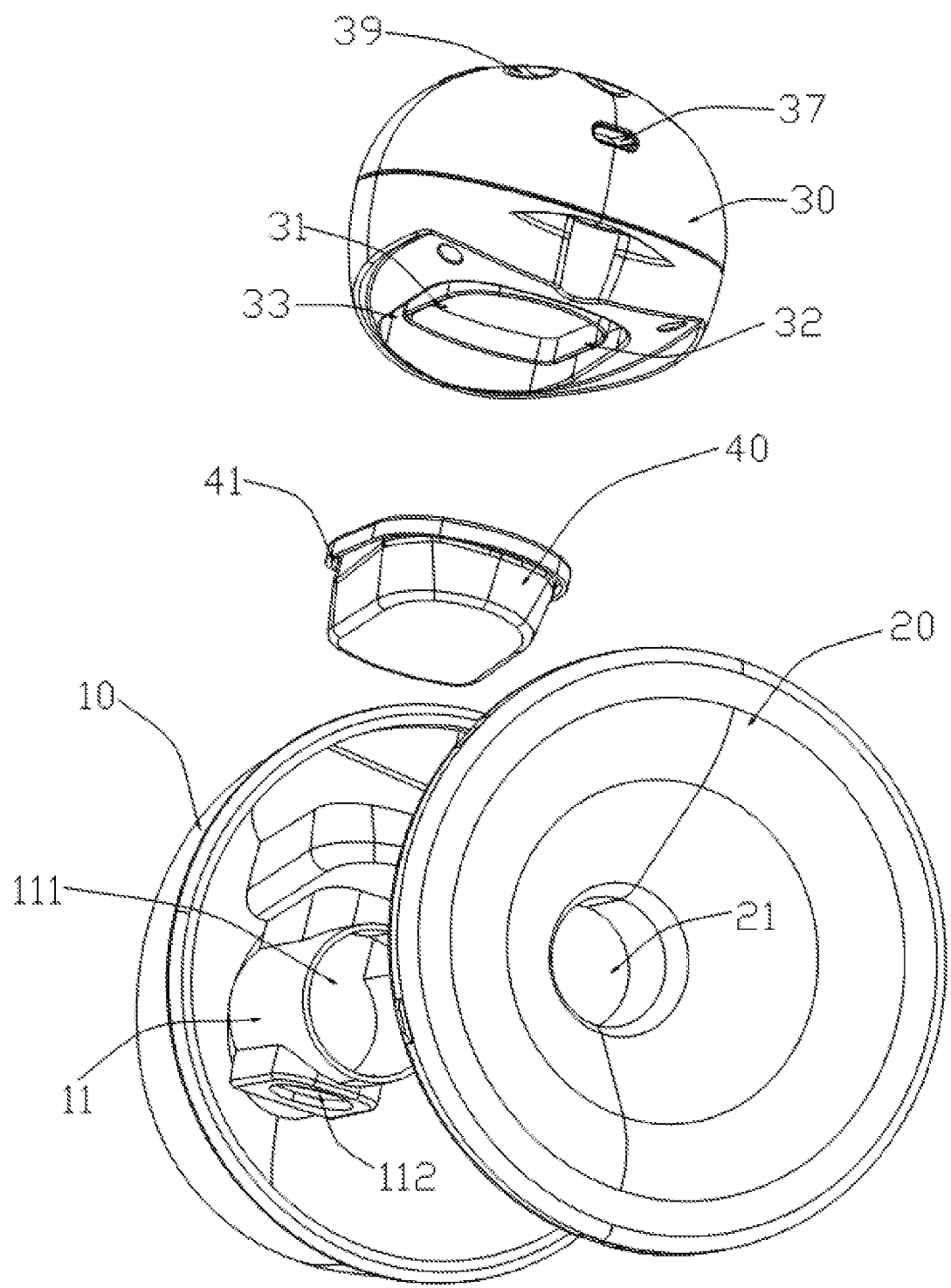
FIG. 4 is another exposed view of the integrated breast pump of FIG. 1.
Figure 5:
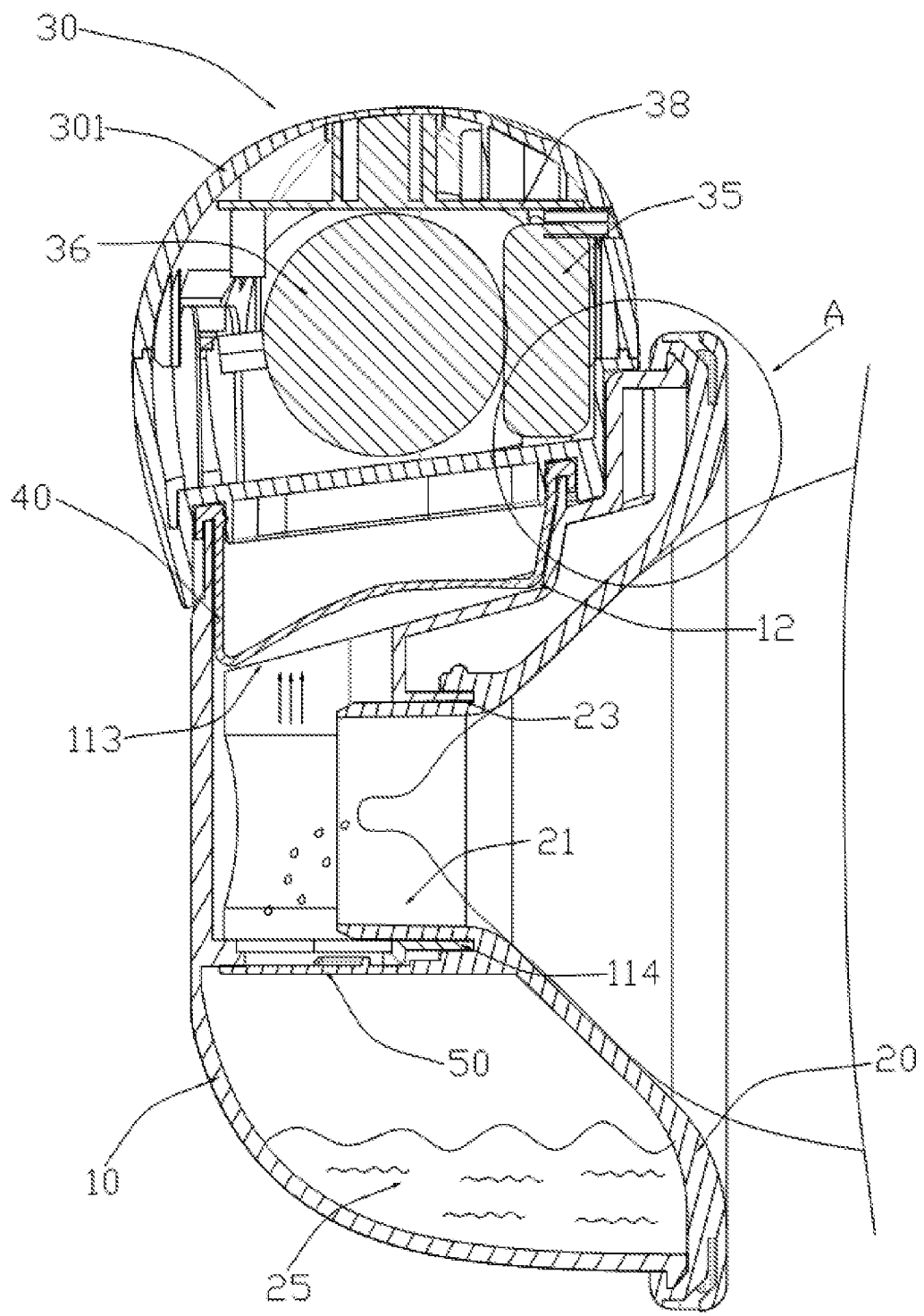
FIG. 5 is a cross-section view of the integrated breast pump of FIG. 1 in a pumping state.
Figure 6:
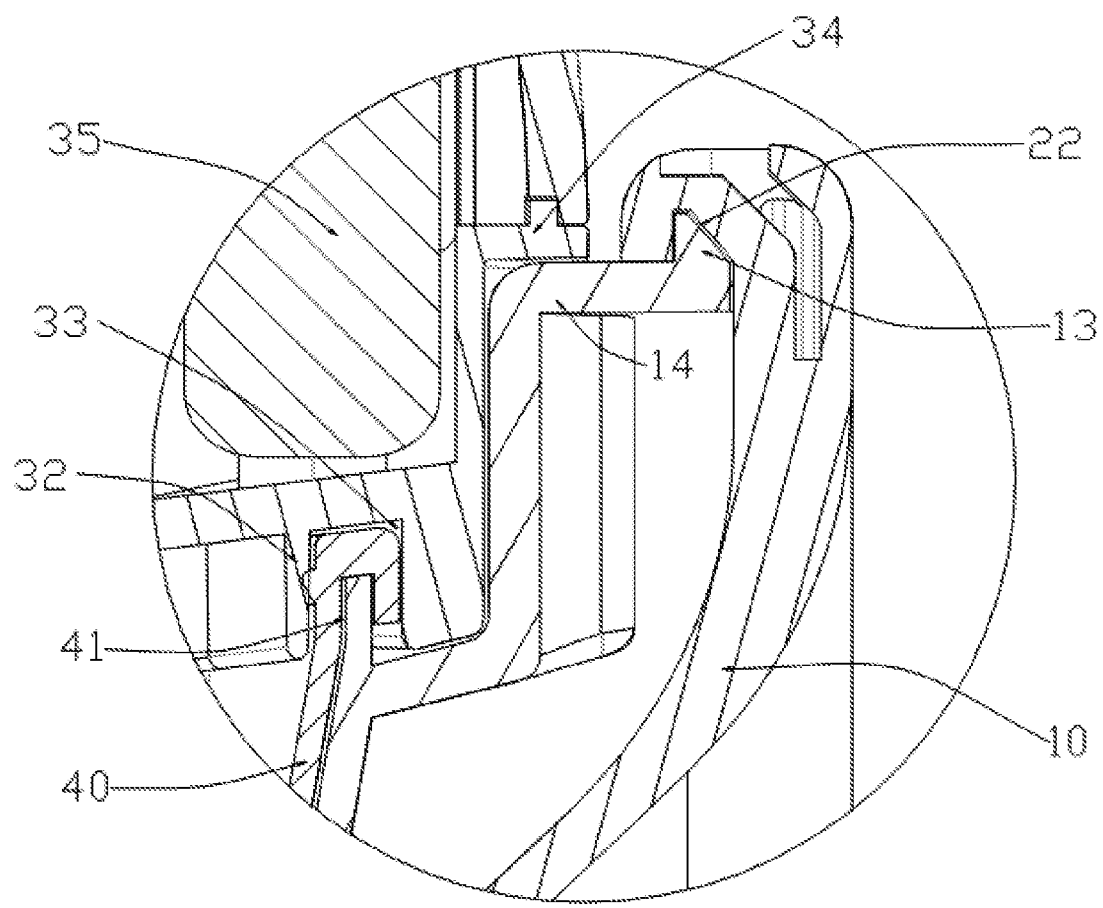
FIG. 6 is an enlarge view of part A of FIG. 5.
Figure 7:
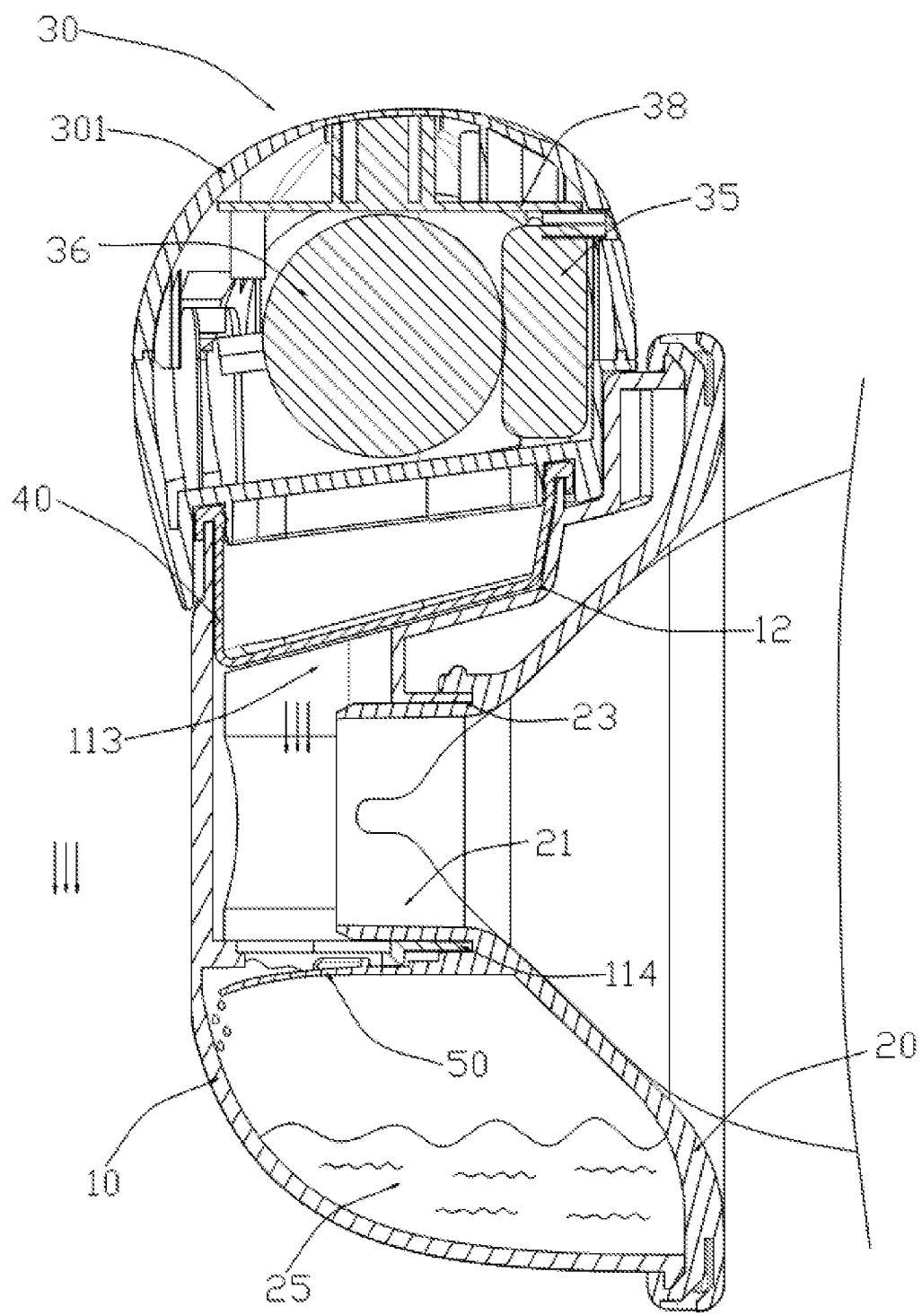
FIG. 7 is a cross-section view of the integrated breast pump of FIG. 1 in a releasing state.

Referring to FIGS. 1-7, an integrated breast pump includes a housing 10, a triple valve 11 integrated with the housing 10, a breast adapter 20 with a funnel shape, a negative pressure generation device 30, a negative pressure transmission element 40 and an one-way valve 50.

The triple valve 11 is integrated with the housing 10, the triple valve 11 includes a liquid inlet 111, a liquid outlet 112 and a negative pressure port 113.

The breast adapter 20 includes a liquid guiding outlet 21 communicating with the liquid inlet 111, and the breast adapter 20 is detachably connected with housing 10.

The negative pressure generation device 30 includes a pumping port 31 configured for providing negative pressure periodically. The negative pressure generation device 30 is detachably connected with housing 10, and the pumping port 31 is disposed towards the negative pressure port 113.

The negative pressure transmission element 40 is disposed in the negative pressure port 113. The negative pressure transmission element 40 communicates with the pumping port 31 and is configured for generating deformation periodically according to the negative pressure.

The one-way valve 50 is connected with the liquid outlet 112.

Through the above structure, the triple valve 11 is integrated with the housing 10, so that the integrated breast pump has a compact and stable structure. A bottom surface of the funnel shaped breast adapter 20 can contact with a breast of a user to bring comfortable experience, and an upper surface of the funnel shaped breast adapter 20 and an inner surface of the housing 10 form a liquid accommodation space 25. The liquid accommodation space 25 can accommodate breast milk, there is no need to use a bottle for accommodating breast milk, such that the integrated breast pump has a high space utilization and a small size. The negative pressure generation device 30 is connected with housing 10, the negative pressure transmission element 40 can transmit the negative pressure periodically, there is no need to use guiding pipes, thus it is convenience to carry and use. It can be understood, the integrated breast pump has a simple and compact structure, a reasonable design, and a small size, it is easy to carry and use, user experience can be improved.

In the embodiment, a surface of the housing 10 includes an accommodating groove 12, the negative pressure port 113 is disposed on a bottom part of the accommodating groove 12, and the negative pressure transmission element 40 is disposed in the accommodating groove 12. Through the above structure, the negative pressure transmission element 40 is disposed in the accommodating groove 12, and the negative pressure transmission element 40 can be fixed and avoid moving. The accommodating groove 12 is disposed on the surface of the housing 10 to save space, thus the structure of the integrated breast pump can be optimized and the size of the integrated breast pump can be reduced.

In the embodiment, an edge of the negative pressure transmission element 40 includes a first restriction groove 41, and a side wall of the accommodating groove 12 is inserted into the first restriction groove 41. Through the above structure, the side wall of the accommodating groove 12 is inserted into the first restriction groove 41, airtightness of the integrated breast pump can be improved, the negative pressure transmission element 40 and the accommodating groove 12 can be connected tightly. Furthermore, an inserting depth can be determined to ensure a stable connection between the negative pressure transmission element 40, the accommodating groove 12 and the pumping port 31, so as to improve the airtightness of the integrated breast pump.

In the embodiment, a surface of the negative pressure generation device 30 includes a fixing block 32, a second restriction groove 33 is formed between the fixing block 32 and a housing of the negative pressure generation device 30, and a side wall of the first restriction groove 41 is fixed in the second restriction groove 33. Through the above structure, the side wall of the first restriction groove 41 is fixed in the second restriction groove 33, such that the negative pressure generation device 30 can be stably connected with the housing 10 and the negative pressure transmission element 40, thus the airtightness of the integrated breast pump can be improved, the periodical negative pressure generated by the negative pressure generation device 30 can be provided to the negative pressure transmission element 40 stably so as to pump breast milk and massage the breast of the user, and use efficiency of the integrated breast pump can be improved. Moreover, the side wall of the first restriction groove 41 is elastic, the side wall of the first restriction groove 41 is fixed in the second restriction groove 33 so as to connect the negative pressure generation device 30 and the housing 10, there is no need other connection structure and it is easy to detach the negative pressure generation device 30 from the housing 10.

In the embodiment, the one-way valve 50 is disposed on an upper surface of the breast adapter 20 and protrudes from the upper surface of the breast adapter 20. When the breast adapter 20 is connected with the housing 10, the one-way valve 50 covers the liquid outlet 112. Through the above structure, the one-way valve 50 is disposed on an upper surface of the breast adapter 20 and integrated with the breast adapter 20, when the breast adapter 20 is connected with the housing 10 and the liquid guiding outlet 21 communicates with the liquid inlet 111, the one-way valve 50 cover the liquid outlet 112. The one-way valve 50 is integrated with the breast adapter 20, assemble steps and components number of the integrated breast pump can be reduced, such that it is easy to assemble the integrated breast pump, and the airtightness of the integrated breast pump can be improved. Moreover, the one-way valve 50 can be opened and closed periodically, the breast milk can flow into the liquid accommodation space 25 stably.

In the embodiment, a first restriction block 13 is disposed on an edge of the housing 10 and protrudes from the edge of the housing 10, a third restriction groove 22 is disposed on an edge of the breast adapter 20, and the first restriction block 13 is inserted in the third restriction groove 22. Through the above structure, the housing 10 and the breast adapter 20 can be detached from each other easily, such that it is convenience to use and clean the integrated breast pump. Moreover, the airtightness of the integrated breast pump can be ensured to prevent the breast milk of the liquid accommodation space 25 from flowing out, and the user experience can be improved.

In the embodiment, a fourth restriction groove 14 is disposed on an upper surface of the breast adapter 34, a second restriction block 114 is disposed on a surface of the triple valve 11, and the second restriction block 114 is inserted in the fourth restriction groove 14. Through the above structure, the second restriction block 114 is inserted in the fourth restriction groove 14, the stable connection and the airtightness between the liquid guiding port 21 and the liquid inlet 111 can be ensured. Moreover, the position of the breast adapter 20 can be restricted so as to avoid wrong operation of the user to destroy the integrated breast pump or the connection between the breast adapter 34 and the triple valve 11, and the user experience can be improved.

In the embodiment, a third restriction block 14 is disposed on the housing 10, a restriction platform 34 is disposed on a surface of the negative pressure generation device 30, and the third restriction block 14 abuts against the restriction platform 34. Through the above structure, the third restriction block 14 abuts against the restriction platform 34 so as to restrict relative position of the housing 10 and the negative pressure generation device 30, ensure stable connection between the housing 10 and the negative pressure generation device 30, it can be prevented, and prevent excessive user force to damage the housing 10 and/or the negative pressure generation device 30 during inserting process.

In the embodiment, the negative pressure generation device 30 includes an accommodation housing 301, a battery 35 and a pump 36, the pump 36 is electrically connected to the battery 35, and the battery 35 and the pump 36 are disposed in the accommodation housing 301. Through the above structure, the battery 35 can effectively provide electric energy for the integrated breast pump and can be used without connecting to the mains, making the integrated breast pump convenient to use and carry. Preferably, the battery is rechargeable and can be reused to improve resource utilization and reduce pollution.

In the embodiment, a charging port 37 is disposed on a surface of the accommodation housing 301, and the charging port 37 is electrically connected to the battery 35. Through the above structure, the charging port 37 is electrically connected to the battery 35, the user can connect the battery 35 to the mains, so as to charge the battery 35 easily, improve battery life and optimize the user experience.

In the embodiment, the negative pressure generation device 30 also includes a control board 38 and at least one button 39. The control board 38 is disposed in the accommodation housing 301, and the control board 38 is electrically connected to the battery 35 and the pump 36. The button 39 is disposed on the surface of the accommodation housing 301, and the button 39 is electrically connected to the control board 38. Through the above structure, the button 39 is electrically connected to the control board 38, it is easy to realize human-machine interaction, the user can control working states of the integrated breast pump through the button 39, such as open or close the integrated breast pump, adjust the working mode of the integrated breast pump, set work time, user experience can be improved and more choices can be provided to the user.

In the embodiment, the outer surface of the housing 10 is curved so that the outer surface of the housing 10 can fit on an inner surface of a bra of the user. Through the above structure, the curved outer surface can be attached to the inner surface of the bra, which is convenient for the user to put the integrated breast pump into the bra for use to free users' hands, thus it is convenience to use, and the integrated breast pump has beautiful appearance.

In the embodiment, the breast adapter 20 is made of silicone. Through the above structure, the silicone breast adapter 20 has flexibility, can be easily installed or removed, and it has inertia, will not cause skin allergy, for long use time, not easy oxidation damage and long service life.

In the embodiment, the negative pressure transmission element 40 is made of silicone. Through the above structure, the silicone negative pressure transmission element 40 has flexibility to effectively deform and reset with the periodical negative pressure, effectively transfer the negative pressure to a nipple of the breast, improve pumping force of the integrated breast pump, and optimize the user experience.

Finally, it should be noted that above embodiments are merely used for illustrating the technical solutions of the disclosure, rather than limiting the disclosure; though the disclosure is illustrated in detail with reference to the aforementioned embodiments, it should be understood by those of ordinary skill in the art that modifications may still be made on the technical solutions disclosed in the aforementioned respective embodiments, or equivalent substitutions may be made to a part of technical features thereof; and these modifications or substitutions do not make the essence of the corresponding technical solutions depart from the spirit and scope of the technical solutions of the respective embodiments of the disclosure.

What is claimed is:

1. An integrated breast pump, comprising
a housing;
a triple valve integrated with the housing, the triple valve comprising a liquid inlet, a liquid outlet and a negative pressure port;
a breast adapter with a funnel shape, the breast adapter comprising a liquid guiding outlet, the breast adapter detachably connected with housing, the liquid guiding outlet communicating with the liquid inlet;
a negative pressure generation device comprising a pumping port configured for providing negative pressure periodically, the negative pressure generation device detachably connected with housing, the pumping port disposed towards the negative pressure port;
a deformable membrane disposed in the negative pressure port, the deformable membrane communicating with the pumping port and configured for generating deformation periodically according to the negative pressure; and
an one-way valve connected with the liquid outlet,
wherein a surface of the housing comprises an accommodating groove, the negative pressure port is disposed on a bottom part of the accommodating groove, the deformable membrane is disposed in the accommodating groove, an edge of the deformable membrane comprises a first restriction groove, and a side wall of the accommodating groove is inserted into the first restriction groove.

2. The integrated breast pump according to claim 1, wherein a surface of the negative pressure generation device comprises a fixing block, a second restriction groove is formed between the fixing block and a housing of the negative pressure generation device, and a side wall of the first restriction groove is fixed in the second restriction groove.

3. The integrated breast pump according to claim 1, wherein the one-way valve is disposed on an upper surface of the breast adapter and protrudes from the upper surface of the breast adapter, and when the breast adapter is connected with the housing, the one-way valve covers the liquid outlet.

4. The integrated breast pump according to claim 1, wherein a first restriction block is disposed on an edge of the housing and protrudes from the edge of the housing, a third restriction groove is disposed on an edge of the breast adapter, and the first restriction block is inserted in the third restriction groove.

5. The integrated breast pump according to claim 1, wherein a fourth restriction groove is disposed on an upper surface of the breast adapter, a second restriction block is disposed on a surface of the triple valve, and the second restriction block is inserted in the fourth restriction groove.

6. The integrated breast pump according to claim 1, wherein a third restriction block is disposed on the housing, a restriction platform is disposed on a surface of the negative pressure generation device, and the third restriction block abuts against the restriction platform.

7. The integrated breast pump according to claim 1, wherein the negative pressure generation device comprises an accommodation housing, a battery and a pump, the pump is electrically connected to the battery, and the battery and the pump are disposed in the accommodation housing.

8. He integrated breast pump according to claim 7, wherein a charging port is disposed on a surface of the accommodation housing, and the charging port is electrically connected to the battery.

9. The integrated breast pump according to claim 7, wherein the negative pressure generation device comprises a control board and at least one button, the control board is disposed in the accommodation housing, and the control board is electrically connected to the battery and the pump, the button is disposed on the surface of the accommodation housing, and the button is electrically connected to the control board.

10. The integrated breast pump according to claim 1, wherein the one-way valve is integrated with the breast adapter.

11. The integrated breast pump according to claim 1, wherein an outer surface of the housing is curved so that the outer surface of the housing is able to fit on an inner surface of a bra of the user.

12. He integrated breast pump according to claim 1, wherein the breast adapter is made of silicone; the deformable membrane is made of silicone.

13. An integrated breast pump, comprising
a housing;
a triple valve integrated with the housing, the triple valve comprising a liquid inlet, a liquid outlet and a negative pressure port;
a breast adapter with a funnel shape, the breast adapter comprising a liquid guiding outlet, the breast adapter detachably connected with housing, and a liquid accommodation space formed by the breast adapter and the housing, the liquid guiding outlet communicating with the liquid inlet;
a negative pressure generation device comprising a pumping port configured for providing negative pressure, the negative pressure generation device detachably connected with housing, the pumping port disposed towards the negative pressure port;
a deformable membrane disposed in the negative pressure port, the deformable membrane communicating with the pumping port and configured for generating deformation according to the negative pressure; and
an one-way valve connected between the liquid outlet and the liquid accommodation space, wherein the one-way valve is disposed on an upper surface of the breast adapter and protrudes from the upper surface of the breast adapter, and when the breast adapter is connected with the housing, the one-way valve covers the liquid outlet.

14. The integrated breast pump according to claim 13, wherein a surface of the housing comprises an accommodating groove, the negative pressure port is disposed on a bottom part of the accommodating groove, and the deformable membrane is disposed in the accommodating groove.

15. The integrated breast pump according to claim 14, wherein an edge of the deformable membrane comprises a first restriction groove, and a side wall of the accommodating groove is inserted into the first restriction groove.

16. The integrated breast pump according to claim 15, wherein a surface of the negative pressure generation device comprises a fixing block, a second restriction groove is formed between the fixing block and a housing of the negative pressure generation device, and a side wall of the first restriction groove is fixed in the second restriction groove.

17. The integrated breast pump according to claim 13, wherein a first restriction block is disposed on an edge of the housing and protrudes from the edge of the housing, a third restriction groove is disposed on an edge of the breast adapter, and the first restriction block is inserted in the third restriction groove; a fourth restriction groove is disposed on an upper surface of the breast adapter, a second restriction block is disposed on a surface of the triple valve, the second restriction block is inserted in the fourth restriction groove; a third restriction block is disposed on the housing, a restriction platform is disposed on a surface of the negative pressure generation device, and the third restriction block abuts against the restriction platform.

* * * * *